United States Patent [19]

Horikoshi et al.

[11] 4,303,787
[45] Dec. 1, 1981

[54] PROCESS FOR RECOVERING CYCLODEXTRINS

[75] Inventors: Koki Horikoshi, Tokyo; Mikio Yamamoto, Asaka; Nobuyuki Nakamura, Kunitachi; Masanobu Kawano, Sendai, all of Japan

[73] Assignees: Rikagaku Kenkyusho, Wako; Nihon Shokuhini Kako Co., Ltd., Marunouchi, both of Japan

[21] Appl. No.: 152,673

[22] Filed: May 23, 1980

[30] Foreign Application Priority Data

Jun. 1, 1979 [JP] Japan .................................. 54/68589

[51] Int. Cl.³ ............................................. C08B 37/16
[52] U.S. Cl. .................................................... 536/103
[58] Field of Search ................................ 536/103, 112

[56] References Cited

U.S. PATENT DOCUMENTS

| | | | |
|---|---|---|---|
| 2,768,097 | 10/1956 | Novak et al. | 536/112 |
| 3,002,823 | 10/1961 | Flodin et al. | 536/103 |
| 3,420,788 | 1/1969 | Solms | 536/103 |
| 3,425,910 | 2/1969 | Armbruster et al. | 435/97 |
| 3,541,077 | 11/1970 | Armbruster | 536/103 |
| 3,923,598 | 12/1975 | Horikoshi | 426/661 |
| 4,024,334 | 5/1977 | Chandler et al. | 536/65 |
| 4,135,977 | 1/1979 | Horikoshi et al. | 435/202 |

FOREIGN PATENT DOCUMENTS 52-25043  8/1975  Japan .................................. 536/103

*Primary Examiner*—Paul R. Michl
*Attorney, Agent, or Firm*—Bucknam and Archer

[57] ABSTRACT

The present invention relates to a novel process for recovering cyclodextrins, characterized in that a solution containing cyclodextrins as well as starches, dextrins, reducing sugars and the like is brought into contact with a hydrophobic, synthetic adsorption resin comprising a porous polymer to adsorb only cyclodextrins, the cyclodextrins thus adsorbed being eluted thereafter with water while being heated to separate and recover said cyclodextrins.

8 Claims, No Drawings

PROCESS FOR RECOVERING CYCLODEXTRINS

BACKGROUND OF THE INVENTION (1) Field of the Invention

The present invention relates to a novel process for recovering cyclodextrins.

Cyclodextrins are hydrolyzates obtained by reacting some gelatinized or liquefied starches with cyclodextrin glycosyltransferase. They are generally obtained by using cyclodextrin glycosyltransferase which is produced by microorganisms such as *Bacillus macerans*, *Bacillus circulans* and the like, or alkalophilic bacteria discovered by the inventors (See "Enzyme Handbook" edited by Shiro Akabori, published by Asakura Shoten (1966); Japanese Pat. No. 886,583, Japanese Patent Publication No. 31223/1978, U.S. Pat. No. 3,923,598, British Pat. No. 1,459,654 and French Pat. No. 74.37001). Cyclodextrins are non-reducing dextrins which have a crownlike structure wherein 6 to 12 glucose units are cyclically combined with one another by α-1,4-glucosidic linkage. It has recently been reported that some of such cyclodextrins have some branched structures wherein glucose units are combined by α-1,6-glucosidic linkage to form branched cyclodextrins. However, α-cyclodextrin, β-cyclodextrin and γ-cyclodextrin which consist of 6, 7 and 8 glucose units, respectively, are useful for industrial purpose. The cyclodextrin molecule has a doughnut-like shape and the interior of the hollow space formed by the molecule is in a hydrophobic atmosphere. On the other hand, the exterior and the opening of the hollow space are in a hydrophilic atmosphere. Such a specific structure of the cyclodextrin molecule is intimately concerned with the inclusion phenomenon thereof. The hollow space sizes of α-, β-, and γ-cyclodextrin molecules are known to be about 6 Å, 8 Å and 10 Å respectively. As mentioned above, the cyclodextrin molecule includes some specific molecules the sizes of which conform to the hollow space size of the cyclodextrin molecule. Accordingly, cyclodextrins are widely usable in foods, medicines, cosmetics, agricultural chemicals and the like, and new applications thereof are expected.

(2) Description of the Prior Art

As described above, various processes for preparing cyclodextrins have been proposed. In conventional processes for preparing cyclodextrins, some gelatinized or liquefied starches are reacted with cyclodextrin glycosyltransferase, an organic solvent is added to the resulting starch hydrolyzates containing cyclodextrins to precipitate cyclodextrins, and the objective cyclodextrins in the hydrolyzates are separated from acyclic dextrins mixture. However, according to this process, the use of harmful organic solvents such as trichloroethylene, tetrachloroethane, bromobenzene, toluene or the like is inevitable, so that this process is undesirable in view of environmental sanitation laws which have become stricter in recent years. In addition, it is also disadvantageous from both the economical and industrial points of view.

In aother proposed process, the above-mentioned starch hydrolyzates containing cyclodextrins are reacted with a saccharified enzyme such as glucoamylase which hardly hydrolyzes cyclodextrins, thereby to hydrolyze acylic mixtures contained in the hydrolyzates to convert them into glucose, after which organic solvents such as ethanol, acetone or the like are added to the mixed sugar solution to selectively precipitate cyclodextrins, the cyclodextrins thus precipitated being separated thereafter (see "Starch Science" (DENPUN-KAGAKU) Vol. 22, No. 1, pp. 6-10 (1975)).

In order to separate cyclodextrins effectively, it is desirable that the enzyme acts on the starch under a condition where the concentration is high. However, under such a condition, it has been found that obtaining a homogeneous gelatinization of starch is difficult and that the working thereof is very difficult due to its high viscosity. On the other hand, the use of low concentration starch also has many disadvantages because complicated means or expensive reagents are necessary to precipitate and separate cyclodextrins and at the same time, considerable costs are incurred to concentrate a sugar solution. Thus, in order to overcome these disadvantages a process for producing and separating cyclodextrins has been proposed, which is characterized in that cyclodextrin glycosyltransferase is reacted with a liquefied starch solution of a high concentration obtained by liquefying starch according to a conventional process, for example, by causing a small amount of α-amylase or acid to act on a starting starch solution (see Japanese Patent Publication No. 2380/1971).

However, organic solvents are used to precipitate produced cyclodextrins in all processes as described above, and the cyclodextrins thus obtained can not be utilized for medicines, foods and the like due to the toxicity of the solvents, which is the fundamental disadvantage in those processes.

CROSS REFERENCE TO RELATED APPLICATION

We have previously discovered a novel process for producing crystalline cyclodextrin without using any organic solvents as mentioned above and have obtained patents for the process (see Japanese Pat. No. 914,137 (Japanese Patent Publication No. 43897/1977), U.S. Pat. No. 4,135,977, British Pat. No. 1,459,654 and French Pat. No. 74.37001). According to this process, cyclodextrin glycosyltransferase produced by a microorganism belonging to Bacillus sp. and having an optimum pH on the alkaline side is caused to act on starch. Acyclic dextrins in the reaction mixture are then hydrolyzed, and the mixture thus treated is concentrated to yield a concentrate containing at least 40% cyclodextrins. Thereafter a small amount of cyclodextrins is added to the concentrate as a seed to precipitate cyclodextrins.

Another process has also been proposed as a non-organic solvent process for recovering cyclodextrins (see Japanese Patent Disclosure No. 136889/1976). In this process, a mixed solution containing cyclodextrins and reducing sugars is brought into contact with OH type-anion exchange resin to adsorb only reducing sugars, and cyclodextrins not adsorbed are separated from reducing sugars. This process is excellent as a novel non-organic solvent process for recovering cyclodextrins. However, a low concentration of cyclodextrins in the resulting solution requires a further step to concentrate the solution to precipitate and isolate cyclodextrins, so that the yield of the final product is low.

SUMMARY OF THE INVENTION

We carried out further research on a non-organic solvent process for recovering cyclodextrins as described above and completed the present process for recovering cyclodextrins, characterized in that a solution containing cyclodextrins as well as starches, dextrins, reducing sugars and the like, for example, starch hydrolyzates containing cyclodextrins, a filtrate obtained by filtering a solution containing β-cyclodextrin, or a sugar solution obtained by treating the starch hydrolyzates or the filtrate with enzyme and containing mainly cyclodextrins and reducing sugars, is brought into contact with a synthetic adsorption resin comprising a porous polymer to adsorb only cyclodextrins and the cyclodextrins thus adsorbed are eluted thereafter with water while heating to separate cyclodextrins.

Thus, highly pure α-, β-, γ- and the other type of cyclodextrins, or if desired, only α-cyclodextrin, are obtained in a high yield by the process of the present invention. No organic solvents are used in the present process, so that, this process does not include any of the problems found in the known processes based on the harmful organic solvents used therein.

DETAILED DESCRIPTION OF THE PREFERRED EMBODIMENTS

The process of the present invention will now be described in detail.

The present invention relates to a novel process for recovering cyclodextrins, characterized in that a solution containing cyclodextrins as well as starches, dextrins, reducing sugars and the like, for example, starch hydrolyzates obtained by reacting some gelatinized or liquefied starches with cyclodextrin glycosyltransferase and containing cyclodextrins, a filtrate obtained by filtering said hydrolyzates containing β-cyclodextrin, or a sugar solution obtained by reacting the hydrolyzates or the filtrate with a saccharified enzyme incapable of hydrolyzing cyclodextrins, or hardly capable thereby to hydrolyze acyclic dextrins therein, and containing mainly cyclodextrins and reducing sugars, is brought into contact with a synthetic adsorption resin comprising a porous polymer to adsorb only cyclodextrins, and the cyclodextrins thus adsorbed are eluted thereafter with water to separate them from reducing sugars. The starches employed as starting material in the present invention include those starches such as potato starch, sweet potato starch, corn starch or the like which are readily and commercially available, or other various materials containing starch.

Prior to reacting them with cyclodextrin glycosyltransferase, these starches suspended in water are liquefied by reacting with bacterial α-amylase, or acids, or stirring with water while heating. In general, the concentration of these starches in the liquid may suitably be in the range of from 2% to 40% by weight. It is necessary to adjust the pH value of the resulting liquified starch to the optimum pH of cyclodextrin glycosyltransferase. For example, when the enzyme obtained from *Bacillus macerans* is used, the liquified pH may be in the range of from 5.0 to 7.0, preferably from 5.5 to 6.0 and when the enzyme produced by alkalophilic bacteria as described above is used, it may be in the range of from 5.0 to 10.5, preferably from 7.0 to 9.0.

Suitable cyclodextrin glycosyltransferases include the known cyclodextrin glycosyltransferases produced by *Bacillus macerans, Bacillus circulans, Bacillus megaterium, Bacillus stearothermofilus, Klebsiella pneumoniae* or the like, or the cyclodextrin glycosyltransferases produced by alkalophilic bacteria as mentioned above, for example, Bacillus sp. No. 38-2 (ATCC 21783), Bacillus sp. No. 135 (ATCC 21595), Bacillus sp. No. 169 (ATCC 21594), Bacillus sp. No. 13 (ATCC 31006) and Bacillus sp. No. 17-1 (ATCC 31007), wherein ATCC: the American Type Culture Collection, IAM: Institute of Applied Microbiology, University of Tokyo, IFO: Institute for Fermentation, Osaka, FERM: Fermentation Research Institute, Agency of Industrial Science and Technology, Ministry of International Trade and Industry, Japan. All of them are "unrestricted deposits". In addition, the enzymes may be employed in the form of a pure or crude enzyme.

According to the present invention, the liquified starch is reacted with the cyclodextrin glycosyltransferase under the conditions of the optimum pH to form mainly α-, β- and γ-cyclodextrins. The mixture is then concentrated, if necessary. Starch hydrolyzatesa thus obtained containing cyclodextrins, or a filtrate obtained by filtering a β-cyclodextrin containing solution obtained from the non organic solvent process (Japanese Pat. No. 914,137) can be used as it stands in a subsequent separation process. In addition, a reaction mixture obtained by reacting the hydrolyzates or the filtrate with a saccharified enzyme incapable or hardly capable of hydrolyzing cyclodextrins thereby to convert acylic dextrins into reducing sugars, or a reaction mixture obtained by reacting the hydrolyzates or the filtrate with a saccharified enzyme incapable or hardly capable of hydrolyzing α-cyclodextrin thereby to convert β- and γ-cyclodextrins and acyclic dextrins mixture into reducing sugars, can also be employed. The saccharified enzymes used in the process include, in the former case, exo-type saccharified enzymes such as glucoamylase, β-amylase, pullulanase and the like and bacterial liquefied type α-amylase and, in the latter case, bacterial saccharified type α-amylase, α-amylase produced by mold and the like. Among these saccharified enzymes, glucoamylase, β-amylase and pullulanase can not hydrolyze cyclodextrins at all, while bacterial saccarified type α-amylase can hardly hydrolyze α-cyclodextrin but can completely hydrolyze β- and γ-cyclodextrins into reducing sugars.

In a process for separating cyclodextrins from the hydrolyzates or the filtrate thus obtained, or a mixed sugar solution containing cyclodextrins and reducing sugars obtained by reacting the hydrolyzates or the filtrate with an enzyme, the hydrolyzates and the filtrate may be passed through a column charged with a synthetic adsorption resin, as it stands. However, the viscosity of the hydrolyzates and the filtrate is preferably reduced to facilitate the operation of the resin charged column. A treatment with a saccharified enzyme as mentioned above is desirable for reducing the viscosity. In this process for reducing viscosity, saccharified enzymes, for example, glucoamylase or bacterial liquefied type α-amylase to mainly recover α-, β- and γ-cyclodextrins, and bacterial saccharified type α-amylase to recover only α-cyclodextrin, may be used to advantage. Further, in the treatment with the latter bacterial saccharified type α-amylase, it is necessary to completely hydrolyze β- and γ-cyclodextrins other than α-cyclodextrin while it is unnecessary to completely convert the remaining linear and branched dextrins into reducing sugars.

In the present invention, the solution containing cyclodextrins, for example, the hydrolyzates, the filtrate or the mixed sugar solution obtained by enzymatic treatment thereof and containing cyclodextrins and reducing sugars, is brought into contact with a synthetic adsorption resin comprising a porous polymer to adsorb only cyclodextrins. For example, the solution may be continuously passed through the column charged with the resin from the top to the bottom. Through this contact, cyclodextrins contained in the downward stream are selectively and completely adsorbed on the resin. On the other hand, reducing sugars and the remaining acyclic dextrins contained in the downward stream are not adsorbed at all and flow out of the column quantitatively. It should be noted that while the downward stream system has been explained above, the upward stream system can also be applied to the process of the present invention.

The solution is continuously passed through the column until the synthetic adsorption resin is saturated, and water instead of the solution is subsequently passed through the column to wash out reducing sugars not adsorbed within the column. After the adsorption resin is saturated, a mixed fraction of cyclodextrins and reducing sugars which are not adsorbed may be recovered and recycled. Further, the initial fraction of reducing sugars may be utilized to recover reducing sugars therefrom or as a solution of reducing sugars.

In the above operation of passing the solution, through the column, the velocity of the solution flowing into the column is intimately related to the diffusion rate of cyclodextrin toward the inside of the adsorption resin particles within the column, that is, the concentration of cyclodextrin adjacent to the adsorption resin particles per unit time and volume. Thus, the higher the cyclodextrin concentration in a solution passed through a column, the lower the flow velocity of the solution. For example, when the filtrate obtained by filtering β-cyclodextrin solution and containing 30% of sugars in all and 20% of cyclodextrins based on the total weight of sugars is being passed through the column, SV may be practically allowed to be about 1.

Further, the cyclodextrins containing solution passed through the adsorption resin column may theoretically have a high concentration. However, considering channeling within the column due to the high viscosity of the solution and the specific gravity of the adsorption resin and the solution, the concentration of the solution may suitably be less than 30% sugar in all.

Furthermore, the adsorption resin has no functional radical as included in an ion exchange resin and so, no secondary reaction occurs. Accordingly, the temperature at which the solution passes into the column is not especially limited. However, adsorbed cyclodextrins are generally eluted while heating, at preferably less than 50° C.

As mentioned above, only cyclodextrins are selectively adsorbed on the adsorption resin by passing the hydrolyzates, the filtrate or the mixed sugar solution obtained by treating the hydrolyzates of the filtrate with an enzyme and containing cyclodextrins and reducing sugars, into a column charged with the adsorption resin. Cyclodextrins adsorbed on the adsorption resin are eluted with water while heating to separate the cyclodextrins.

Accordingly, after the resin is saturated with cyclodextrins by passing the solution through the column, the remaining sugars not adsorbed on the resin are washed out with water at room temperature and then, hot water is passed into the column or water is passed into the column while elevating the temperature within the column by passing hot water or water vapor through a jacket placed around the column, whereby adsorbed cyclodextrins are eluted. When a temperature gradient is used, α- and γ-cyclodextrins first, and then, β-cyclodextrin are eluted separately. In addition, the sequence in which α- and γ-cyclodextrins are eluted and the temperature at which each of the cyclodextrins is eluted depend on the properties of the adsorption resin to be used. Therefore, they may suitably be determined by the properties of the adsorption resin. And, as mentioned above, cyclodextrins adsorbed on the adsorption resin can easily be eluted and separated with hot water or water vapor. The adsorption resin can therefore be recycled and used again in the adsoption process without a regenerating process which is necessary with an ion exchange resin. This is one of the advantages of the present invention.

The adsorption process of the present invention and the adsorption resin to be used in the process will now be described in detail.

In general, the adsorption phenomenon on a solid means that a force works to fix a substance to be adsorbed on to a surface of the solid. There are several types of interaction between the substance to be adsorbed and the solid such as a hydrophobic bond, dipole interaction and a hydrogen bond. It is also known that a hydrophobic or nonpolar molecule or its moiety is easily attracted to a hydrophobic surface, and that a hydrophilic or polar substance is easily attracted to a hydrophilic or polar surface. We have conducted further research into synthetic adsorption resin having a property of selectively adsorbing only cyclodextrins in the cyclodextrins containing solution, while paying close attention to general properties of a hydrophobic adsorbent having an ability to separate hydrophobic organic substances from a solution containing a hydrophilic substance which is not to be adsorbed by resin. We have experimentally confirmed for the first time that when the solution containing cyclodextrins is brought into contact with a hydrophobic adsorbent comprising a porous polymer having pores into which liquid water can not enter, cyclodextrins having an internal surface which is hydrophobic can reach the surface to be adsorbed through the pores and can be adsorbed there. Further, we have found that excellent adsorbability can be obtained by suitably selecting pore size and surface area of the adsorbent comprising a porous polymer.

Thus, without adhering to theory, it is considered that the cyclodextrin molecule, which has reached the resin surface, includes a lipophilic group on the resin surface due to hydrophobicity inside the molecule, thereby to form a clathrate compound, so that cyclodextrins are adsorbed on the resin surface.

A synthetic adsorption resin employed in the process of the present invention is a synthetic adsorbent having a huge net structure and is a resin comprising a porous polymer in the form of sphere or plate or in the amorphous form. Such resin is a hydrophobic organic porous resin comprising, for example, styrene-divinylbenzene copolymer, ethyl-vinylbenzene copolymer, fluoroplastic, silicone resin, polyolefinic resin and the like. Particularly, styrene-divinylbenzene copolymer is useful.

Among these polymers, for example, styrene-divinylbenzene copolymer in the spherical form can be obtained by suspending and polymerizing styrene and divinylbenzene (crosslinking agent) in water as a porous polymer having a large number of micropores. In the present invention, porous styrene-divinylbenzene copolymer having more than about 100 m$^2$/g of a specific surface is particularly useful.

Such copolymer as described above has a very low polarity, a large internal surface, and the properties that water vapor can be adsorbed but liquid water can not enter the pores.

In the present invention, the composition of the copolymer and the specific surface have no particular limitation. Generally, the polymer having less than about 1,000 m²/g of specific surface may suitably be used. The porosity of the polymer is preferably in the range of from 40% to 90%. A porosity of less than 35% results in a decrease in surface and an increase in weight, while a porosity of more than 95% results in deformation of the polymer particle when charging a column, with the final result that there is an increase in water pressure loss. Hence, both of the above porosity ranges are undesirable.

In addition, the copolymer as mentioned above may be used in the form of a hydrophobic derivative treated with silane or the like. With respect to the surface area of the adsorbent, the pore size thereof is important. According to the present invention, it is necessary to have apertures of a sufficient and proper size to enable the cyclodextrins to migrate up to the adsorption surface through such apertures and at the same time to be adsorbed.

There is an inversely proportional relation between surface area and pore size. Namely, the smaller the pore size of the adsorbent, the larger the surface area. Therefore, considering the molecular weights ($\alpha$:973, $\beta$:1135, $\gamma$:1297) and sizes of cyclodextrins, the adsorbent having about from 100 to 1,000 m²/g of specific surface and proper size may preferably be selected.

Porous styrene-divinylbenzene copolymer adsorbent having properties as described above includes, for example, AMBERLITE XAD-2 and -4 (Rhom & Haas Co. U.S.A.), DIAION-HP (Mitsubishi Chemical Ind. Ltd. JAPAN) and PORAPAK-N -P, -Q, -R and PORAPAK-QS (Waters Associates, Inc.).

In the present invention, as mentioned above, elution is performed with water while heating. Most of the elution of the adsorbent substance is generally performed with such suitable organic solvents, bases, or acids that interact with the surface of the adsorbent. On the contrary, in the process of the present invention, elution of adsorbed cyclodextrins can easily and properly be performed with hot water or water vapor without using such elutes as organic solvents at all.

As described above, organic solvents are not used at all in any processes for preparing starting materials, for adsorbing and for eluting in the present invention. It can be said that this process in which the objective cyclodextrin can be obtained on an industrial scale is an epoch making one.

As mentioned above in detail, according to the process of the present invention, a desired cyclodextrin can be separated from the cyclodextrin containing solution and recovered, as it is, that is, without using any organic solvents. The process of the present invention also has a remarkable feature that the object can be achieved in a high yield without any additional treatment processes at all.

Cyclodextrins obtained by the process of the present invention may further be treated with, according to a well-known method, another adsorption resin which adsorbs reducing sugars but not cyclodextrins, giving purer cyclodextrin.

The process of the invention will be described with reference to the following examples.

REFERENCE EXAMPLE 1

Potato starch solution (4% (W/V), 15 l, starch content: 600 grams) was adjusted to pH 5.5 and was homogeneously gelatinized at a temperature of 125° C. for 30 minutes and, was then rapidly cooled.

A culture medium containing 1% of corn steep liquor, 1% of soluble starch, 0.5% of ammonium sulfate, and 0.5% of calcium carbonate was heated at a temperature of 120° C. for 30 minutes to sterilize, and was cooled. Thereafter, the medium was inoculated with Bacillus macerans (IAM 1243) and was cultivated while shaking at a temperature of 37° C. for 2 days. The cultivated medium was then filtered or centrifuged to remove the microorganisms, giving a crude enzyme solution (15 units/ml). The enzyme solution (800 ml) was added to the gelatinized starch solution which was then diluted to obtain 2% solution of starch (total volume: 30 l). The mixture was held at 40° C. for 70 hours and then heated at 100° C. for 5 minutes to inactivate the enzyme. The weight of the cyclodextrins produced was 32% with respect to starch.

REFERENCE EXAMPLE 2

Potato starch solution (4% (W/V), 15 l, starch content: 600 grams) was adjusted with sodium hydroxide to pH 9.0 and was then homogeneously gelatinized at 125° C. for 30 minutes. After being cooled to 60° C., the enzyme produced by Bacillus sp. No. 38-2 (ATCC 21783) (600 mg, 10,000 units/ml. Meito Sangyo Co., Ltd.) was added to said gelatinized starch solution, which was reacted at 60° C. for 30 hours. After the completion of the reaction, the reaction mixture was heated at 100° C. for 5 minutes to inactivate the enzyme, and thereafter cooled to 55° C. and adjusted to pH 5.0 with hydrochloric acid. To the mixture, 900 mg of glucoamylase (2,000 units/grams, GSA-1, Amano Pharm. Co., Ltd.) was added and further reacted for 20 hours. The reaction mixture was conventionally decolored with activated carbon, filtered, desalted and concentrated to 50% of solid content. Thereafter, 500 mg of $\beta$-cyclodextrin was added to the concentrate and the mixture was allowed to stand overnight in a cold chamber. The resulting precipitated $\beta$-cyclodextrin was removed by filtration to obtain a filtrate.

EXAMPLE 1

The filtrate obtained in Reference Example 2 (containing 20% by weight of cyclodextrins based on the total weight of sugars) was adjusted to a concentration of 20% (W/V). The adjusted solution (30 ml) was passed, by downward stream method, through a column charged with 100 ml of AMBERLITE XAD-2, at a rate of SV=1 at 20° C., and then 500 ml of water was passed through the column to wash out the non-adsorbed substances.

This effluent was concentrated to about 80 ml of sugar solution containing about 6% of sugar. The sugar solution was analyzed by high performance liquid chlomatography (DU PONT 830, column: WATERS $\mu$BONDAPAK CH (4 mm$^\phi$×30 cm), solvent: acetonitrile: water=70:30, flow: 1 ml/minute, Temperature: 40° C.) and it was found that the sugar solution contained 4.7 grams of glucose, maltose, maltotriose and maltooligosaccharide. The yield was 97.9% based on reducing sugars in effective running solution.

Then, maintaining the column at about 85° C. and eluting with water at a rate of SV=0.5, 45 ml of fraction containing about 2% cyclodextrins was obtained. The fraction was analyzed by high performance liquid chlomatography and it was found that the fraction contained α-, β- and γ-cyclodextrins. No peaks based on reducing sugars were observed. The solid content in the fraction was 1.1 grams and the yield was 91.7% based on cyclodextrins in the effective solution passing through the column.

EXAMPLE 2

The fraction containing 2% cyclodextrins (α:34.8%, β:46.1%, γ:19.1%) (1,250 ml) obtained in Example 1 was concentrated to about 50% concentration and crystallized to obtain about 7.5 grams of β-cyclodextrin. The filtrate was concentrated to about 30%, adjusted to pH 5.0, and bacterial saccharified type α-amylase (Daiwa Kasei Ind. Co., Ltd.) was then added to the filtrate in a quantity of 0.5% based on the solid weight in the filtrate, after which the mixture was maintained at 40° C. for 24 hours. The saccharified solution was found to contain reducing sugars mainly comprising α-cyclodextrin, glucose, maltose, and maltotriese. After the completion of the reaction, the saccharified solution thus obtained was heated. This was decolored with activated carbon and filtered to obtain 60 ml of 25% (W/V) solution containing α-cyclodextrin. The sugar composition of the saccharified solution was 45% of reducing sugars and 55% of α-cyclodextrin.

Then, the saccharified solution was cooled to room temperature and was passed through a column charged with one 1 of AMBERLITE XAD-4 by downward stream method at a rate of SV=0.75, and 3 l of water was passed through the column to wash out the nonadsorbed substances. Then, a mixed solution of both effluents was concentrated to obtain about 90 ml of about 7.5% reducing sugars solution. The solid content of this solution was 6.7 grams and the yield was 99.3% based on reducing sugars in the saccharified solution.

Then, maintaining the column at about 80° C. and eluting with water at a rate of SV=0.5, 300 ml of fraction containing about 2.5% α-cyclodextrin was obtained. The solid content in the fraction was about 7.5 grams and the yield was 90.9% based on α-cyclodextrin in the effective solution passing through the column.

EXAMPLE 3

Starch hydrolyzates containing cyclodextrins obtained in Reference Example 1 (2% (W/V), 32% cyclodextrins based on the total weight of sugars) (1 l) was passed through a column charged with 500 ml of AMBERLITE XAD-2 by downward stream method at a rate of SV=1 at 20° C., and the column was washed with 2 l of water. The effluent was then concentrated to obtain 150 ml of about 9% remaining starch solution. The solid content in this solution was 13.5 grams and the yield was 99.3% based on the remaining starch substances in the effective solution passing through the column.

Then, maintaining the column at about 85° C. and eluting with water at a rate of SV=0.5, 300 ml of a fraction containing 2% cyclodextrins was obtained. The solid content in the fraction was 6.0 grams and the yield was 93.8% based on the cyclodextrins in the effective solution passing through the column.

The fraction containing cyclodextrins was analyzed by the above-mentioned high performance liquid chlomatography, and the following result was obtained, α:68.4%, β:24.4%, γ:7.2%.

EXAMPLE 4

Maintaining a 1% soluble starch solution containing 10 mM calcium carbonate (pH 7.5, 500 ml) at 50° C., the solution was added with 20 mg enzyme (600 units/g) produced by Bacillus sp. No. 38-2 (ATCC 21783), and was reacted for one hour. Then, the reaction solution was passed through a column charged with 250 ml of AMBERLITE XAD-4 and maintained at 50° C. at a rate of SV=0.5, and the effluent was returned into the reaction solution. This process was continued for 48 hours. Thereafter, water was passed through the column to completely wash out the remaining starch substances. Then, maintaining the column at 85° C. by passing hot water through a jacket of the column, water was passed through the column to obtain a 160 ml fraction containing 2% cyclodextrins. The solid content of the fraction was 3.2 grams and the yield was 64% based on the total weight of sugars in the effective solution passing through the column.

The fraction containing cyclodextrins was analyzed with the above mentioned high performance liquid chlomatography and the following result was obtained, α:27.0%, β:57.1%, γ:15.9%.

EXAMPLE 5

To 250 ml of 4% potato starch gelatinized solution obtained in Reference Example 1, was added 15 ml of crude enzyme solution (15 units/ml) produced by Bacillus macerans (IAM 1243) obtained also in Reference Example 1. The pH was adjusted to 5.5, and the total volume was taken as 500 ml. Then, using a column charged with 250 ml of AMBERLITE XAD-2, the procedure as described in Example 4 was performed at 40° C. for 72 hours. After washing the column, water was passed through the column to obtain a 210 ml fraction containing about 2% cyclodextrins. The solid content of the fraction was 4.2 grams and the yield was 42% based on the total weight of sugars in the effective solution passing through the column.

The fraction containing cyclodextrins was analyzed by the above mentioned high performance liquid chlomatography and the following result was obtained, α:74.7%, β:19.1%, γ:6.2%.

What we claim is:

1. A process for recovering cyclodextrins wherein a solution containing cyclodextrins as well as starches, dextrins, reducing sugars is brought into contact with a hydrophobic, synthetic adsorption resin comprising a porous polymer to absorb only cyclodextrins, said polymer having no functional radical and having pores into which liquid water cannot enter, after which said adsorbed cyclodextrins are eluted.

2. A process according to claim 1 wherein said synthetic adsorption resin comprises a porous styrene-divinylbenzene copolymer having a specific surface of greater than 100 m²/g.

3. A process according to claim 1 wherein said elution step is carried out with water while heating.

4. A process according to claim 3 wherein said elution step is carried out with water while heating to obtain each of the cyclodextrins contained therein.

5. A process according to claim 1 wherein said solution is any one of the following:
   a solution containing starch hydrolyzates obtained by reaction some gelatinized or liquefied starches with cyclodextrin glycosyltransferase, a filtrate obtained by filtering said hydrolyzates to remove β-cyclodextrin, or, a solution containing saccharified products comprising cyclodextrins and reducing sugars, said products are obtained by reacting said hydrolyzates or said filtrate with a saccharified enzyme incapable or hardly capable of hydrolyzing cyclodextrins thereby to hydrolyze acyclic dextrins mixture therein.

6. A process according to claim 5 wherein said filtrate is obtained from starch hydrolyzates by crystallizing β-cyclodextrin therein without using any organic solvents.

7. A process according to claim 5 wherein said solution containing starch hydrolyzates and said filtrate are a solution containing saccharified products comprising mainly α-cyclodextrin and reducing sugars, said products are obtained by reacting said hydrolyzates or said filtrate with a sacchrified enzyme incapable or hardly capable of hydrolyzing α-cyclodextrin thereby the hydrolyze cyclodextrins other than α-cyclodextrin and acylic dextrins mixture therein.

8. The process according to claim 1, wherein said polymer has less than 1000 $m^2/g$ specific surface and the porosity is 40–90%.

* * * * *